US006426105B1

(12) United States Patent
Palta et al.

(10) Patent No.: US 6,426,105 B1
(45) Date of Patent: Jul. 30, 2002

(54) USE OF LYSOPHOSPHATIDYLETHANOLAMINE (18.1) AND LYSOPHOSPHATIDYLINOSITOL TO RETARD SENESCENCE AND TO ENHANCE FRUIT RIPENING

(75) Inventors: Jiwan Paul Palta; Stephen Beungtae Ryu, both of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/254,039

(22) PCT Filed: Nov. 9, 1998

(86) PCT No.: PCT/US98/23714

§ 371 (c)(1),
(2), (4) Date: May 24, 1999

(87) PCT Pub. No.: WO99/23889

PCT Pub. Date: May 20, 1999

Related U.S. Application Data

(60) Provisional application No. 60/064,784, filed on Nov. 10, 1997.

(51) Int. Cl.[7] .............................................. A23L 1/212
(52) U.S. Cl. ..................... 426/331; 426/331; 426/333
(58) Field of Search .................. 504/116; 426/331, 426/333, 102, 615, 616, 270

(56) References Cited

U.S. PATENT DOCUMENTS

| 5,110,341 A | 5/1992 | Palta et al. ................... 71/86 |
| 5,126,155 A | 6/1992 | Palta et al. ................. 426/331 |
| 5,521,223 A | 5/1996 | Piazza et al. ............... 514/785 |

FOREIGN PATENT DOCUMENTS

| JP | 930192425 | 8/1993 |
| SU | 87372490 | 12/1987 |

OTHER PUBLICATIONS

Ag et al. (Physiologia Plantarum, (1993), vol. 87, No. 4, pp. 515–521, ISSn: 0031–9317). 1993.*

Farag, Karim M. et al., Use of lysophosphatidylethanolamine, a natural lipid, to retard tomato leaf and fruit senescence, *Physiologia Plantarum*, 97:515–521, (1993).

Farag, Karim M. et al., Use of Natural Lipids to Accelerate Ripening Ripening and Enchance Storage Life of Tomato Fruit with and without Ethephon, *HortTechnology*, 3(1):62–65, (1993).

Ryu, Stephen B. et al., Inhibition of phospholipase D by lysophosphatidylethanolamine, a lipid–derived senescence retardant, *Proc. Natl. Acad. Sci. USA*, 94:12717–12721, (1997).

Ryu, Stephen B. et al., "Expression of Phospholipase D during Castor Bean Leaf Senesence[1]", *Plant Physiol.*, (1995), pp. 713–719, vol. 108.

Kaur, Navjot, et al., "Postharvest Dip in a Natural Lipid, Lysophosphatidylethanolamine, May Prolong Vase Life of Snapdragon Flowers", *HortScience* 32(5):888–890, (1997).

* cited by examiner

*Primary Examiner*—Sabiha Qazi
(74) *Attorney, Agent, or Firm*—Gardner, Carton & Douglas

(57) ABSTRACT

The present invention relates to a method of enhancing fruit ripening and stability and of delaying senescence in fruit and other plant tissues. This method consists of applying an effective amount of a lysophospholipid, such as lysophosphatidylethanolamine (18:1) (hereinafter referred to as "LPE (18:1)") or lysophosphatidylinositol (hereinafter referred to as "LPI") to the fruit and other plant tissues. Lysophospholipids such as LPE (18:1) and LPI were found to be superior to other lysophospholipids in delaying senescence and in inhibiting phospholipase D, a key enzyme in mediating membrane deterioration during of plant senescence. LPE (18:1) and LPI are naturally occurring and environmentally safe. Their use could replace many environmentally toxic compounds that are currently being used to retard senescence of flowers, fruits and leaves and to enhance fruit ripening.

13 Claims, 6 Drawing Sheets

US 6,426,105 B1

Figure 1:
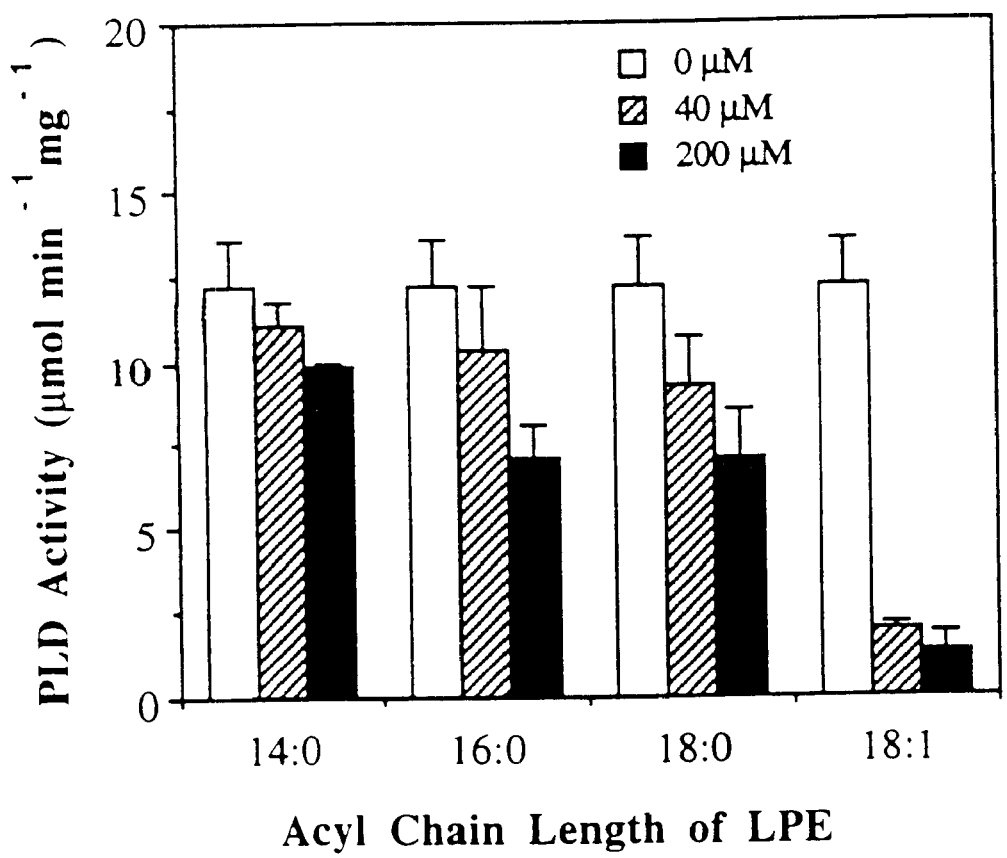

USE OF LYSOPHOSPHATIDYLETHANOLAMINE (18.1) AND LYSOPHOSPHATIDYLINOSITOL TO RETARD SENESCENCE AND TO ENHANCE FRUIT RIPENING

CROSS-REFERENCE TO RELATED APPLICATIONS

This application is a 371 application of PCT/US98/23714, Nov. 9, 1998, which claims priority from U.S. Ser. No. 60/064,784 filed on Nov. 10, 1997.

STATEMENT REGARDING FEDERALLY SPONSORED RESEARCH OR DEVELOPMENT

This invention was made with United States government support awarded by the following agencies: USDA AGRICREE Grant No: 93-37100-8924 and USDA Grant No: 94-34190-1204. The United States has certain rights in this invention.

BACKGROUND OF THE INVENTION

Various chemical and biological agents are currently being used on commercially grown fruit to control the timing of fruit ripening. Such agents can be used for a variety of purposes. One purpose is to synchronize the ripening of fruit to assist in efficient harvesting of fruit from the field. Another purpose is to prevent drop off of fruit so that fruit remain on the plant until the appropriate ripening time period. Another purpose of fruit ripening agents is to enhance color development in the fruit so the fruit has a better and more uniform color as expected by retail consumers of the fruit. In the United States, it is current practice for many types of fruit to be treated with one or more such agents during the cultivation processes.

Some agents previously used for control of fruit ripening are purely synthetic agents found to have desired effects on the fruit in question. Unfortunately, due to issues of both potential toxicity and oncogenicity, several such synthetic chemical fruit ripening agents have either been banned or had their use sharply curtailed due to commercial or consumer resistance to the products. The most popular agent currently being used to enhance fruit ripening is ethephon, a synthetic compound, which is sold under the name of Ethrel, a trademark of Rhone-Poulenc Ag. Co. (Research Triangle Park, N.C.). Although this agent stimulates ripening, it also causes the fruit to soften. Thus, fruit treated with ethephon has a very poor shelf life. There is a critical need for a ripening agent which is environmentally safe and which does not cause fruits to soften. In addition, consumers are willing to pay a premium price for vine ripened fruits. However, vine ripened fruits cannot be transported long distances because these fruits soften and have poor shelf life. Therefore, it would be beneficial to improve the shelf life of vine ripened fruits.

There is also a tremendous interest in the plant industry (especially in the fresh vegetables and cut flower industries) to find an environmentally safe product to retard senescence and promote shelf or vase life. Presently, environmentally toxic compounds such as silver thiosulfate are being used to increase the vase life of cut flowers. However, the use of silver thiosulfate is being curtailed because of environmental concerns. Therefore, it is desired to develop alternatives to silver thiosulfate, which are much more likely to be readily accepted by commercial interests and consuming public.

Lysophosphatidylethanolamines (hereinafter referred to as "LPE") comprise a group of compounds that have shown promise in controlling fruit ripening, enhancing fruit stability during storage, and increasing the shelf life of stored fruit. Methods for using LPE purified from egg (hereinafter referred to as "LPEegg") to enhance fruit ripening and stability are disclosed in U.S. Pat. Nos. 5,126,155 and 5,100,341, which are incorporated by reference herein. LPE is derived from phosphatidylethanolamine, a lipid normally found in cell membranes. Phosphatidylethanolamine is a phospholipid with two fatty acid moieties which is abundant in egg yolk. The removal of one fatty acid from phosphatidylethanolamine by phospholipase $A_2$ yields LPE.

LPE is also naturally present in plant and animal tissue, especially rich in egg yolk and brain tissue. It is available commercially from Avanti Polar Lipids, Inc. (Alabaster, Ala.). There are numerous different fatty acids that can be found in LPE purified from natural sources. The fatty acids can vary in the length of a chain as well as the degree of unsaturation. However, the relative efficacy of various species of LPE and also of different kinds of lysophospholipids other than LPE in the control of fruit ripening and enhancing fruit stability has not been examined.

SUMMARY OF THE INVENTION

The present invention relates to a method of delaying senescence in fruit or plant tissues. The method involves applying to the fruit and other plant tissues, either prior to or after harvest, a composition containing a lysophospholipid and an activating agent. The composition contains an amount of a lysophospholipid that is effective in delaying senescence in fruit and other plant tissues. The preferred lysophospholipid contained in the composition is lysophosphatidylinositol and/or lysophosphatidylethanolamine (18:1). In addition to containing the lysophospholipid, the composition may also contain an activating agent, such as ethanol, tergitol or sylgard 309.

Moreover, the present invention also relates to a method of enhancing the ripening and stability of fruit. The method involves applying to whole plants before harvest, a composition containing a lysophospholipid and an activating agent. The composition contains an amount of lysophospholipid that is effective in enhancing fruit ripening and stability. The preferred lysophospholipid contained in the composition is lysophosphatidylinositol and/or lysophosphatidylethanolamine (18:1). In addition to containing the lysophospholipid, the composition may also contain an activating agent, such as ethanol, tergitol or sylgard 309.

BRIEF DESCRIPTION THE DRAWINGS

FIG. 1. is a graph showing inhibition of partially purified cabbage PLD activity by various concentrations of LPE with different acyl chains.

Figure 2:
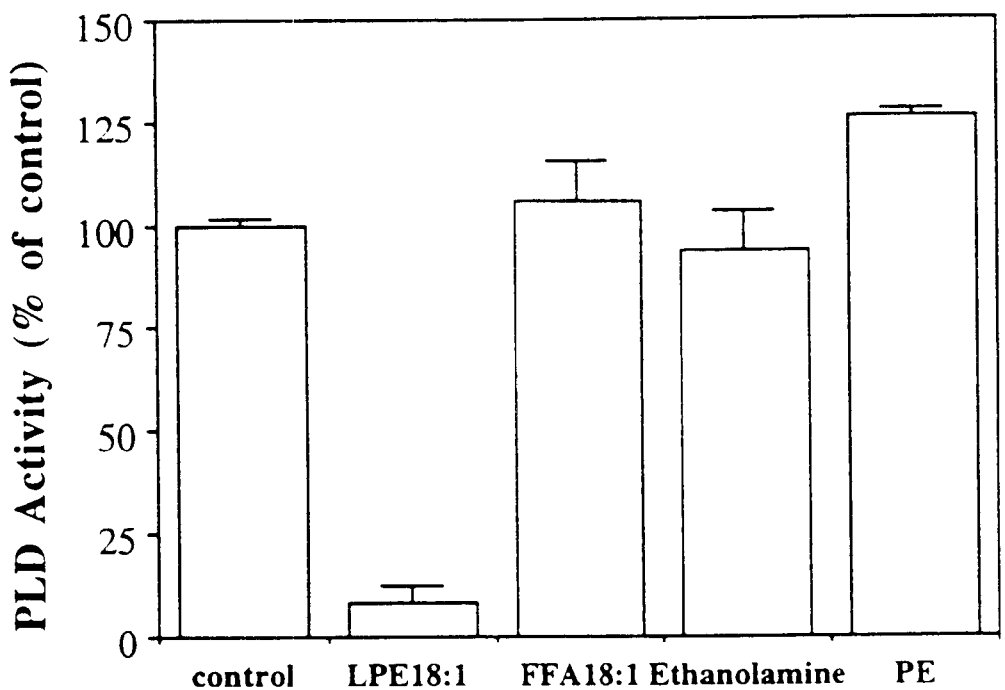

FIG. 2. is graph showing the structural specificity of LPE (18:1) for its inhibition of partially purified cabbage PLD activity.

Figure 3:
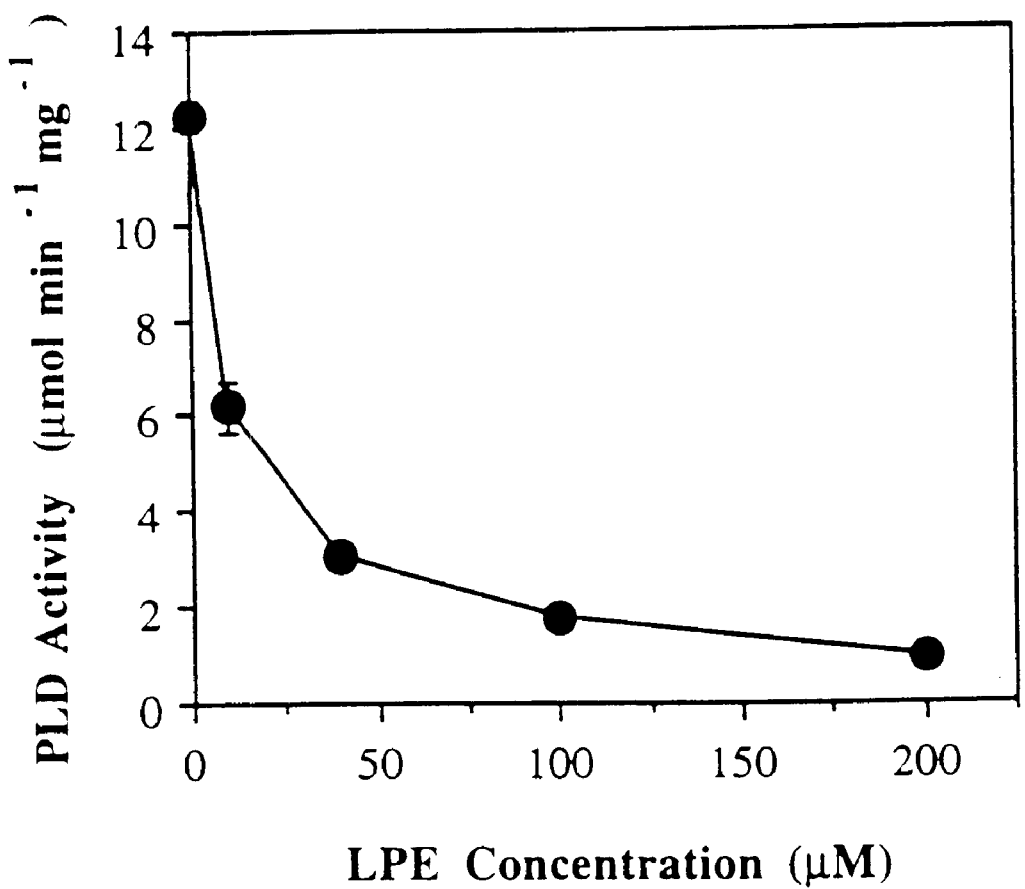

FIG. 3. is a plot showing inhibition of partially purified cabbage PLD activity as a function of LPE concentration.

Figure 4:
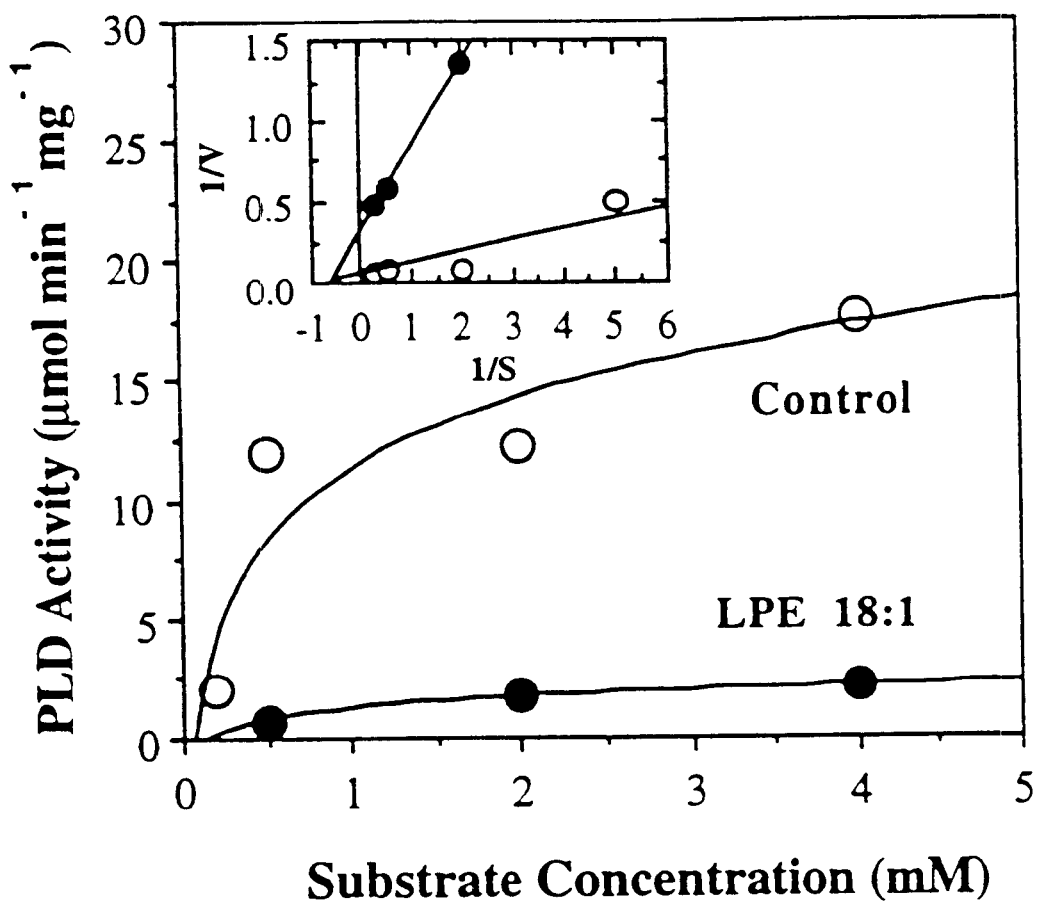

FIG. 4. is a plot showing the effect of substrate concentration on the inhibition of partially purified cabbage PLD by LPE (18:1).

Figure 5:
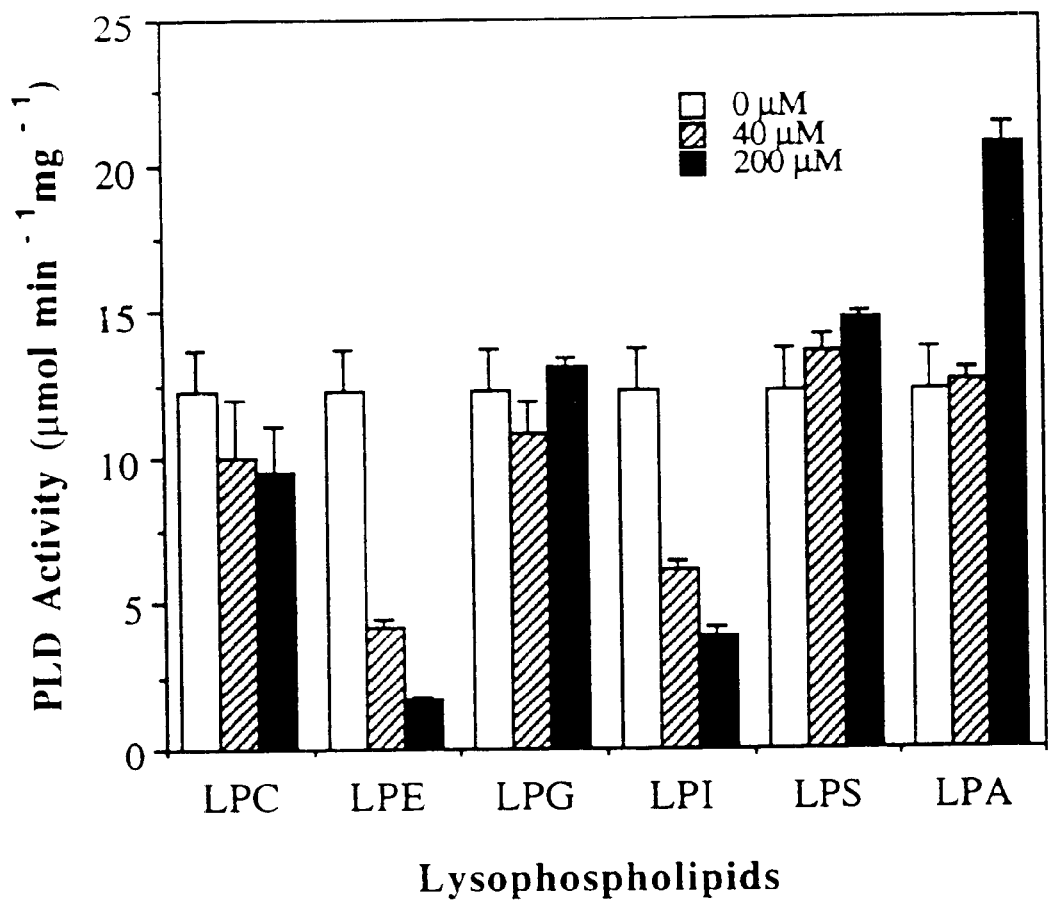

FIG. 5. is a graph showing the effect of different lysophospholipids on partially purified cabbage PLD activity.

Figure 6:
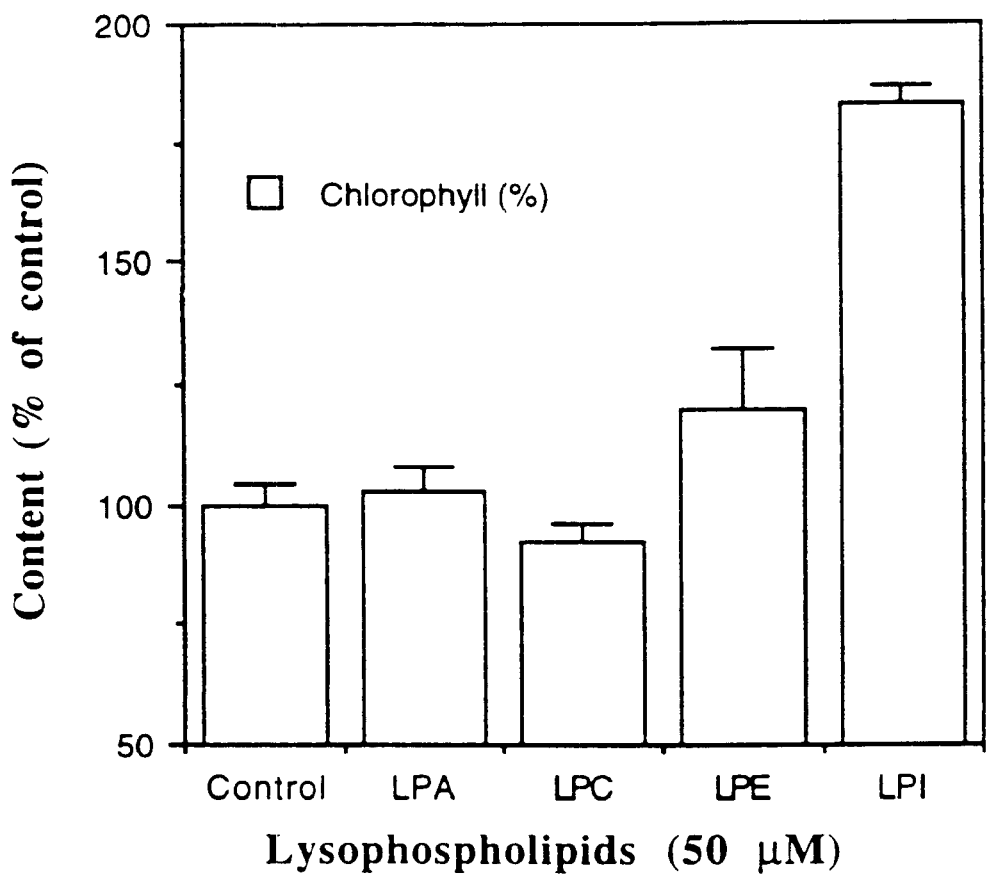

FIG. 6. is a graph showing the relative chlorophyll content of leaves treated with LPA, LPC, LPEegg, or LPI.

DETAILED DESCRIPTION OF THE INVENTION

The present invention relates to a method of enhancing fruit ripening and stability and delaying senesence in fruit and other plant tissues using lysophospholipids, including, but not limited to, LPE (18:1) and/or lysophosphatidylinositol (hereinafter referred to as "LPI"). As used herein, the term "lysophospholipids" refers to derivatives of phospholipids having a single fatty acid removed by phospholipase $A_2$. As used herein, the term, "plant tissues" refers to any part or organ from a live plant. Examples include fruit, flowers, roots, stems, hypocotyls, leaves, petioles, petals, etc.

The method of the present invention involves treating fruit and other plant tissues prior to or after harvest with a composition containing a lysophospholipid having the formula:

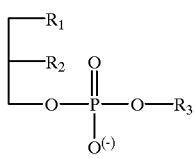

(I)

where $R_1$ is selected from the group consisting of $C_5$–$C_{22}$ acyloxy and $C_5$–$C_{22}$ alkoxy group; $R_2$ is selected from the group consisting of hydrogen, hydroxyl, $C_1$–$C_5$ acyloxy and $C_1$–$C_5$ alkoxy group; and $R_3$ is selected from the group consisting of hydrogen, choline, ethanolamine, glycerol, inositol and serine, wherein $R_1$ and $R_2$ are interchangeable with each other. Preferred compounds having the above-identified formula (1) are LPE (18:1) and LPI.

Preferably, the composition contains an acceptable carrier for the lysophospholipid, such as water. However, other carriers, such as organic solvents, can be used as well. The composition contains an amount of lysophospholipid that is effective in enhancing fruit ripening and stability and in delaying senescence in fruit and other plant tissues. More specifically, the amount of lysophospholipid in the composition can be from about 0.5 to about 1000 mg per 1 liter of the composition, preferably from about 1 to about 500 mg per 1 liter of the composition, more preferably from about 5 to about 250 mg per 1 liter of the composition and even more preferably from about 5 to about 100 mg per 1 liter of the composition. The composition can be applied to the fruit or plant tissues as a spray or simply in liquid form.

In addition to containing the lysophospholipids, the composition can also contain one or more activating compounds. As used herein, the term "activating compounds" refers to agents that enhance wettability, uptake and effectiveness of an active ingredient, which is the lysophospholipid. Examples of activating compounds that can be used in the method of the present invention include ethanol, TERGITOL® (TERGITOL® is a nonylpthenol polyoxyethylene ether. TERGITOL® is a registered Trademark of Union Carbide Chemicals and Plastics Company, Inc., available from Sigma Chemical Company, St. Louis, Mo.) and SYLGARD® 309 (SYLGARD® 309 is 76% siloxylated polyether and 24% of a surfactant mixture. SYLGARD® is a registered trademark and is available from Dow Corning Co., Midland, Mich.). The activating compounds can be present in the composition in the amount of from about 0.05% to about 2% (v/v) of the composition.

The preferred lysophospholipid, LPE (18:1), is a species of LPE having an 18 carbon fatty acid containing a single double bond. LPE (18:1) has been found to be particularly superior to other species of LPE in promoting fruit ripening and delaying senescence of fruit and plant tissues. LPI has been found to be comparable to LPE (18:1) and superior to LPEs other than LPE (18:1) in enhancing fruit ripening and in delaying senescence of fruit and plant tissues.

As disclosed in U.S. Pat. Nos. 5,126,155 and 5,110,341, LPE is effective in enhancing fruit ripening and stability. The exact mechanism by which these effects are achieved is only partially understood. It was disclosed in U.S. Pat. Nos. 5,126,155 and 5,110,341 that LPE was observed to stimulate ethylene production and suppress respiration in fruit. It was speculated that these effects might account for the enhanced ripening and stability of LPE-treated fruit. Delayed senescence of LPE-treated fruit and plant tissues was found to be correlated with reduced leakage of electrolytes through membranes (5). Thus, the inventors suspect that LPE may regulate a key process of membrane deterioration in plant senescence and aging.

Increased leakage of electrolytes during plant senescence has been ascribed to the breakdown of membrane phospholipids (1,2). Reduced leakage of electrolytes in LPE-treated leaves, flowers and postharvest fruits suggests that LPE may protect membrane integrity by inhibiting membrane lipid degradation (3). Based on the kinetics of release of various lipolytic products in vivo and in vitro, phospholipase D (thereinafter referred to as "PLD") has been proposed to mediate the selective degradation of membrane phospholipids, which is a rapid and early event occurring in senescing tissues (4–9). An increase in PLD expression was observed in senescing leaf tissues and the expression of PLD was characterized by complex modes including an increase in membrane-associated PLD, differential expression of PLD variants, and changes in amounts of PLD protein and mRNA (10).

As described herein, the inventors demonstrate that the lysophospholipid LPE can inhibit the activity of partially purified PLD in a highly specific manner in plants. As the following examples below demonstrate, the lysophospholipids LPE (18:1) and LPI are particularly strong inhibitors of PLD. In addition, treatment of plants with LPE (18:1) or LPI is associated with reduced ethylene production. LPI has been found to be particularly effective in delaying senescence in leaves, as evidenced by the high chlorophyll content of LPI-treated senescing leaves, relative to a control as well as compared to LPE or LPC-treated leaves. Consequently, lysophospholipids, such as, but not limited to, LPE (18:1) and LPI are particularly attractive agents for delaying senescence of fruit and plant tissues. The inventors also demonstrate that LPE (18:1) and LPI are particularly effective in enhancing fruit ripening and stability.

By way of example and not of limitation, examples of the present invention will now be given.

EXAMPLE 1
Specific Inhibition of PLD by LPE (18:1) and LPI

EXAMPLE 1a
Chemicals and Plant Materials

Natural lysophospholipids purified from egg yolk, bovine liver, and soybean and synthetic LPE with different acyl chains (14:0, 16:0, 18:0, 18:1) were obtained from Avanti Polar Lipids (Alabaster, Ala.). All other phospholipid chemicals and materials used were obtained from Sigma (St. Louis, Mo.). Phospholipids and fatty acid were dissolved in chloroform:methanol:KOH (1N) (95:5:1, v/v). After water was added, organic solvents were expelled by flowing nitrogen gas. Stock solution concentrations were adjusted to 1 mM with water before being added to the PLD reaction mixture. The LPE solution for treating fruit and plant tissues was prepared in bulk by sonicating LPE powder suspended in water without the use of organic solvents.

Partially purified cabbage PLD, which has commonly been used for investigating the biochemical and physiological aspects of PLD (11,12), was dissolved in 50 mM Tris (pH 8.0) and added to a reaction mixture with a final concentration of 0.6 µg/ml in order to examine the effect of LPE on PLD activity.

In addition to the partially purified cabbage PLD, the inventors also investigated the effect of LPE on the activities of membrane-associated PLD and soluble PLD which were obtained from two plant sources, i.e. cabbage (*Brassica oleracea* L. Blue Vintage) and castor bean (*Ricinus communis* L. cv. Hale). Castor bean plants were grown in plastic pots containing a mixture of vermiculite and parlayed (1:1, v/v), which were subirrigated at 22° C. with Hoagland nutrient solution under cool-white fluorescent lights (150 $\mu$mol min$^{-m}$m$^{-2}$) with a 14-h photoperiod (10). Cabbage was obtained from fresh market.

EXAMPLE 1b
Tissue Fractionation

Fully expanded leaves from two-month-old castor bean plants and cabbage were harvested, quickly frozen in liquid nitrogen, and homogenized with a mortar and pestle chilled on ice (13). An extraction buffer containing 50 mM Tris-HCl (pH 8.0) 10 mM KCl, 1 mM EDTA, 0.5 mM PMSF, and 2 mM DTT was added to the powder samples. After grinding for additional 5 min., the homogenate was centrifuged at 6,000 g for 10 min. to remove debris. The supernatant was centrifuged at 100,000 g for 30 min. to fractionate the extract into soluble and membrane-associated PLD. The resultant supernatant was collected as the soluble fraction and the pellet as the membrane fraction. The membrane fraction was washed once with extract buffer to remove soluble contaminants. The soluble PLD and membrane-associated PLD samples were added to the reaction mixtures at final concentrations of 100 µg/ml and 10 µg/ml, respectively.

EXAMPLE 1c
PLD Activity Assay

The activity of partially purified cabbage PLD was assayed by measuring the phosphorus content contained in phosphatidylethanol (hereinafter referred to as "PEOH") and phosphatidic acid (hereinafter referred to as "PA") released from the substrate phosphatidylcholine (hereinafter referred to as "PC") (13). For this assay, 20 µmol of PC from egg in chloroform was dried under a stream of nitrogen gas. The lipid was emulsified in 1 ml H$_2$O by sonication at room temperature. A standard enzyme assay mixture contained 100 mM Mes/NaOH (pH 6.5), 50 mM CaCl$_2$, 0.5 mM SDS, 20 µl substrate (0.4 µmol PC), 1% ethanol and 20 µl PLD in a total volume of 200 µl (14). The assay mixture was then incubated at 30° C. for 30 min. in the water bath. The reaction was stopped by adding 750 µl chloroform:methanol (1:2). Chloroform (200 µl) was added to the mixture followed by 200 µl of KCl (2M). After vortexing, the chloroform and aqueous phases were separated by centrifugation at 12,000 g for 5 min. The chloroform phase was collected and dried. The dried samples were dissolved in 50 µl of chloroform before they were spotted onto a TLC plate (silica gel G). The plate was developed with solvent of chloroform:methanol:NH$_4$OH (65:35:5). Lipids on plates were visualize by exposure to iodine vapor. Spots corresponding to the lipid standards PEOH, PA and PC were scraped into vials and the amounts were quantitated by measuring phosphorus content as described in Rouser et al. (15). PEOH, the product of transphosphatidylation reaction, was used as the indicator of PLD activity rather than PA, the product of hydrolytic reaction, since the former is not readily metabolized.

The PLD activity associated with the membrane and soluble fractions obtained from cabbage and castor bean tissues were measured by quantifying the release of radiolabeled PEOH and PA from the substrate PC (10). For this purpose, 0.4 µCi of L-3-phosphatidylcholine, 1,2-di[1-C$^{14}$] palmitoyl (Amersham (Arlington Heights, Ill.)) was mixed with 20 µmol PC from egg in chloroform. The assay condition and reaction product separation were the same as described above. Radioactivity in PEOH, PA and PC scraped from the TLC was quantitated by scintillation spectroscopy.

EXAMPLE 1d
LPE Treatment and Fruit Ethylene Production

Postharvest treatment of fruit tissues with LPEegg (which is purified from egg and consists mostly of LPE 16:0 and LPE 18:0) has previously been found to retard senescence and enhance shelf life of fruits (3,16). However, the impact of different acyl chains of LPE on fruit senescence has not been investigated. In the present study, complementary to the effect of different acyl chains of LPE on PLD activity, the inventors investigated the effect of different acyl chains of LPE on ethylene production of cranberry fruits. Fully ripened cranberry fruits (*Vaccinium macrocarpon* Ait. 'Stevens') were harvested during the fall season and kept in a cold room. Randomly selected postharvest cranberry fruits (15 berries per sample) were dipped into LPE solutions with different acyl chains (100 µM) for 30 minutes, then air-dried and left at room temperature (26±2° C.). After two days, berries were incubated in a sealed glass jar for 24 hours in order to measure ethylene production. Ethylene was quantified with a gas chromatograph equipped with a flame ionization detector (Shinadzu 9AM, Shimadzu Corporation, Kyoto, Japan) (3).

EXAMPLE 1e
Effect of Lysophospholipids on Leaf Chlorophyll Content

To evaluate the relative efficacy of various species of lysophospholipids in delaying senescence in leaves, treatment solutions containing lysophosphatidic acid (LPA), lysophosphatidylcholine (LPC),LPE, LPI, or water were applied to leaves. The chlorophyll content of each sample was measured by standard methods (10) after an eight day senescence. The relative chlorophyll contents were expressed as the percentage of the control.

EXAMPLE 1f
Results and Discussion
Inhibition of PLD Activity by LPE with Different Acyl Chains The inventors studied whether LPE, a naturally occurring phospholipid, acts a biologically active lipid mediator by inhibiting PLD activity in vitro in a specific manner. The inhibitory effects of LPE on partially purified cabbage PLD were assayed using PC as substrate. The PLD activity was inhibited by LPE with different acyl chains at the concentrations of 40 and 200 µM (FIG. 1). The extent of inhibition increased with the length and the unsaturation of acyl chains. LPE with an acyl chain of 18:1 was the most effective inhibitor among the tested species and resultant PLD activity was 16% and 11% of the control at the LPE concentrations of 40 and 200 µM, respectively. On the other hand, LPE 14:0, which is seldom present in plant tissues, had very little effect. The effects of LPE with other acyl chains including 18:2 and 18:3 would be interesting to test but these forms of LPE are not commercially available at the present time. A dramatic inhibition of PLD by LPE (18:1), as compared to other LPE molecules tested, suggest that a specific configuration of LPE is needed for this inhibitory effect.

Structural Specificity of LPE (18:1) for Its Inhibition of PLD

The effect of different components of LPE molecules on PLD activity was tested to determine if any structural specificity was necessary for LPE inhibition. The head group (ethanolamine) and acyl chain (18:1 fatty acid) by themselves had no inhibitory effect on PLD activity (FIG. 2). These results indicate that only the intact LPE molecule is capable of inhibiting PLD, and a loss of any structural components results in complete ineffectiveness; thus indicating its structural specificity. In fact, phosphatidylethanolamine (PE) had some stimulatory effect on PLD activity. In the presence of 200 $\mu$M PE, PLD activity was 126% of the control (FIG. 2). Since PE is itself a preferential substrate of PLD (17), the increase in PLD activity might be explained by its direct stimulating effect on PLD and/or a preferential hydrolysis of PE by PLD.

Dose-Dependency and Kinetics of PLD Inhibition by LPE (18:1)

Inhibition of PLD by LPE was dose-dependent (FIG. 3). LPE (18:1) showed a dramatic inhibitory effect at the 10 $\mu$M concentration resulting in 50% activity of the control and a gradual increase of inhibition with increased concentration up to 200 $\mu$M. LPE concentrations of 10 and 200 $\mu$M reflect 0.5 and 10 mol percents of total phospholipid in reaction mixtures, respectively.

In order to characterize inhibition of PLD, the effects of substrate concentration on PLD inhibition were analyzed in the presence and absence of LPE (FIG. 4). Normal assay conditions utilize the saturating concentration of substrate (2 mM PC). The inhibitory effect of LPE (18:1) was maintained even at the 4 mM substrate concentration (FIG. 4). The apparent Km for PLD was 1.7 mM and did not change in the presence of LPE. However, the presence of LPE (18:1) resulted in a dramatic decrease in Vmax (2.9 $\mu$mol min$^{-1}$ mg$^{-1}$ protein), compared to the control (Vmax of 20.0 $\mu$mol min$^{-1}$ mg$^{-1}$ protein). These results suggest non-competitive inhibition of PLD by LPE.

In Situ Inhibition of PLD by LPE (18:1)

Since PLD is present not only in a soluble form in the cytosol but also in a membrane-associated form, the inventors determined in situ inhibition of LPE on membrane-associated PLD extracted from cabbage and castor bean leaves. Specific activities of membrane-associated and soluble cabbage PLD were decreased to 59% and 51% of the control in the presence of LPE (18:1), respectively (Table 1). Membrane-associated and soluble castor bean PLD activities also decreased to 31% and 30% of the control, respectively. These results indicate that both membrane-associated and soluble PLD activities are inhibited by LPE. The inhibition of PLD associated with membrane and soluble fractions was, however, less pronounced than the inhibition of partially purified cabbage PLD by LPE (FIG. 1 and Table 1). This is perhaps due to the presence of some interfering factors or to presence of the other forms of PLD which are less sensitive to LPE. Partial purification of PLD, therefore, has been suggested to be critical in characterizing the regulatory mechanisms of PLD (18). For this reason, in the present study, the inventors have used partially purified cabbage PLD, which is commercially available. However, the observed inhibitory effect of LPE on membrane-associated and soluble PLD extracted from leaf tissues supports the results obtained with partially purified PLD.

TABLE 1

Inhibition of soluble and membrane-associated PLD activities (nmol min$^{-1}$ mg$^{-1}$ protein) by LPE (18:1). Data are mean ±SE of two separate extractions (duplicate experiments from each extraction) prepared from cabbage and castor bean leaves.

|  | Soluble PLD | | Membrane-associated PLD | |
| --- | --- | --- | --- | --- |
|  | Cabbage | Castor Bean | Cabbage | Castor Bean |
| Control | 45.2 ± 3.5 | 10.2 ± 0.1 | 368.8 ± 6.5 | 153.8 ± 8.5 |
| LPE 18:1 (200 $\mu$M) | 23.1 ± 1.6 | 3.1 ± 0.1 | 217.0 ± 13.0 | 47.0 ± 3.6 |
| Ratio |  |  |  |  |
| (LPE/Control) | 0.51 | 0.30 | 0.59 | 0.31 |

Inhibition of Fruit Ethylene Production by LPE with Different Acyl Chains

Previously, LPEegg (extracted from egg yolk) had been found to delay fruit senescence as indicated by lowered rates of ethylene production when compared to the control (3). Since the inventors found that the inhibitory effectiveness of LPE on PLD was dependent on the length and unsaturation of acyl chain of LPE (FIG. 1), the effects of LPE with different acyl chains on fruit senescence were tested. Cranberry fruits were treated with LPE with 14:0, 16:0, 18:0 and 18:1 chain lengths, and ethylene production by these fruits was monitored. The inhibition of ethylene production increased with acyl chain length and the unsaturation of LPE (Table 2). LPE (18:1) resulted in the most dramatic decrease (40%) in ethylene production 2 days after treatment. Interestingly, this pattern of inhibition of ethylene production by various types of LPE was similar to the pattern of inhibition of PLD by various types of LPE (FIG. 1). These results indicate that inhibition of PLD activity and ethylene production is consistently dependent on the acyl chain length and the unsaturation of LPE. These results suggest that LPE (18:1) is superior to other LPE species tested in inhibiting PLD and retarding fruit senescence.

TABLE 2

Inhibition of ethylene production in cranberry fruits by LPE (100 $\mu$M) with different acyl chains. Values are mean ±SE of three replications.

|  | Control | LPE14:0 | LPE16:0 | LPE18:0 | LPE18:1 |
| --- | --- | --- | --- | --- | --- |
| Ethylene (nl hr$^{-1}$g$^{-1}$) | 1.78 ± 0.38 | 1.78 ± 0.11 | 1.65 ± 0.05 | 1.27 ± 0.05 | 1.06 ± 0.13 |
| Relative % | 100 | 100.0 | 92.7 | 71.3 | 59.6 |

Structurally Selective Regulation of PLD by Lysopholipids

To address whether the inhibition of PLD could occur by a wide range of lysophospholipids, the inhibitory effect of LPE on PLD was compared to inhibition by related lysophospholipids present in plant cells (FIG. 5). Lysophosphatidylcholine (hereinafter referred to as "LPC"), lysophosphatidylglycerol (hereinafter referred to as "LPG") and lysophosphatidylserine (hereinafter referred to as "LPS") did not significantly affect on PLD activity. However, LPI showed inhibitory effects somewhat similar to those of LPE. Whereas, lysophosphatidic acid (hereinafter referred to as "LPA") significantly increased PLD activity (FIG. 5). For example, at 200 $\mu$M concentration LPI and LPA, the PLD activity was 31% and 169% of the control, respectively. The only synthetic lysophospholipid tested in FIG. 5 was LPA. All other lysophospholipids were from natural sources containing primarily 16:0 or 18:0 fatty acids. In addition to LPA (16:0) (FIG. 5), the inventors also tested LPA (18:1) and found similar results from the two types of LPA. In the present study, LPE but not LPC had a strong inhibitory effect on PLD (FIG. 5). These results indicate that the regulatory effect of individual lysophospholipids on PLD enzyme is very specific and structurally selective.

In addition to LPE, the results suggest that LPI may also be a lipid mediator for retarding senescence in plants. ps Delayed Leaf Senescence by LPI The chlorophyll content of senescing leaves treated with LPI was found to be much higher than leaves treated with LPA, LPC or LPEegg (FIG. 6). This result indicates that LPI is particularly effective in delaying leaf senescence.

In summary of example 1, to the inventors' knowledge, this is the first study showing a specific inhibitory regulation of PLD by LPE (18:1) and LPI, which directly target the activity of PLD enzyme. This is a significant finding since there are no known specific inhibitors of PLD in plants and animals (19). It has also been shown that treatment of fruit plants with LPE (18:1) reduces ethylene production more than LPE species with shorter acyl chain lengths or a higher degree of saturation. Because both ethylene and PLD are associated with senescence in plants, it is reasonably expected that LPE (18:1) and LPI are particularly effective in delaying senescence in fruit and plant tissues than other species of LPE.

EXAMPLE 2
Retarding Senescence and Enhancing the Shelf-Life of Flowers

Flowering spikes of snapdragon (*Antirrhinum majus* L. cv. Potomac White) were harvested and delivered from a commercial grower overnight (20). Upon receipt, the stem ends of spikes were recut under distilled water and allowed to rehydrate for 2 hrs. After rehydration, spikes were trimmed to a length of 40 cm and the leaves on the lower 18 cm of the spike were removed. This prevented leaves from becoming source of bacterial and fungal contamination in the vase. All spikes were then pooled and randomly selected for treatment. LPE(18:1), LPI and LPEegg were prepared in distilled water. Sonication was used to facilitate dissolution of LPE and other lysophospholipids in water.

For the LPE treatment, the cut end of the spikes were held for 24 hr in a solution of LPE at the different concentrations. Thereafter, they were transferred to distilled water and kept in that water for 3 weeks. Spikes were observed for opening of floral buds and also for symptoms of senescence (wilting and browning). If the flower neck became wilted, the flower was considered to be nonmarketable. A spike was considered marketable as long as it remained turgid (not wilted) and when more than 50% of the florets remained healthy. At the end of the study, the water content of spike leaves was determined as an indicator of turgidity and leaf health by measuring the ratio of fresh versus dry weight.

As shown below in Table 3, LPEegg (LPE purified from egg) treatment was able to retard senescence as compared to control; in the former 37–52% of spikes had wilted while in the control 76% of them had wilted after 7 days of treatment. LPE (18:1) and LPI treatment was particularly effective in increasing vase life of snapdragon flowers; only 30–39% and 15–22% of spikes had wilted, respectively, in these two treatments. LPE (18:1) and LPI not only increased vase life of flower but also improved the sensitivity of the flowers to these lipids. For example, 5 mg/L of LPI and LPE (18:1) yielded more prolonging of flower vase life than did 25 mg/L of LPEegg, indicating that LPI and LPE (18:1) are more active forms among lysophospholipids for the retardation of senescence. Flowers treated with LPI and LPE (18:1) remained marketable up to 13 days while water-treated flowers and LPEegg-treated flowers remained marketable for 4 days and 7 days, respectively. Leaf water content of LPE (18:1)-and LPI-treated spikes was higher than that of LPEegg and water-treated spikes at 18 days after treatment. This data is consistent with the improved shelf-life of flowers treated with LPE (18:1) and LPI. This data support that LPE (18:1) and LPI are superior to LPEegg.

TABLE 3

| Treatment | Spikes with Wilted Flower Florets after 7 days (% of total) Mean ± SE* | Water Content of Leaf after 18 days (Fresh wt/Dry wt) Mean ± SE* | Vase Life ** of Spikes (Days) |
|---|---|---|---|
| Control (water) | 75.5 ± 10.3 | 5.79 ± 0.18 | 4 |
| LPEegg | | | |
| 5 mg/L | 52.3 ± 9.5 | 6.77 ± 0.44 | — |
| 10 | 50.0 ± 15.5 | — | — |
| 25 | 36.7 ± 5.55 | — | 7 |
| LPE18:1 | | | |
| 5 mg/L | 34.5 ± 5.5 | 7.81 ± 0.22 | — |
| 10 | 30.0 ± 5.5 | — | 12 |
| 25 | 38.7 ± 8.5 | — | — |
| LPI | | | |
| 5 mg/L | 21.6 ± 7.0 | 7.57 ± 0.52 | — |
| 10 | 15.0 ± 11.5 | — | 13 |
| 25 | 17.8 ± 7.5 | — | — |

*Date are mean ± SE of two independent experiments. Each experiment was done with 12 spikes per treatment.
** Vase life: Days when > 50% of spikes remained marketable.

Flowering spikes of carnation (*Dianthus caryophyllus* L. cv. White Sim) obtained from a commercial grower were treated with various lipids as described above for snapdragons. As with the snapdragons, LPI and LPE (18:1) at 25 mg/L were superior to LPEegg and control in prolonging the vase life of carnations (Table 4). LPEsoy (LPE purified from soybean) also gave better shelf-life than LPEegg (LPE purified from egg). LPEsoy consists of 64% unsaturated LPE, such as LPE (18:1), LPE (18:2), and LPE (18:3) and 30% saturated LPE such as LPE (16:0) and LPE (18:0), and 2% LPI (available from Avanti Polar Lipids, Inc., Alabaster, Ala.), while LPEegg contains mostly (>94%) saturated LPE such as LPE (16:0) and LPE (18:0). This result supports the inventors' conclusion that LPE (18:1) and LPI are superior to other LPE species in prolonging the vase life of flowers.

TABLE 4

| Treatment | Marketable Flowers after 6 days of treatment (% of total) *Mean ± SE |
|---|---|
| Control (water) | 27.5 ± 3.3 |
| LPEegg | 30.8 ± 3.3 |
| LPE18:1 | 41.7 ± 8.3 |
| LPI | 44.2 ± 8.3 |
| LPEsoy | 41.7 ± 8.3 |

*Date are mean ± SE of 36 flowers per treatment. (9 flowers/Replications)

EXAMPLE 3
Retardation of Fruit Senescence

Mature green fruits of tomato (*Lycopersicon esculentum* cv. H9144) were harvested from three month old plants. Harvested fruits were dipped in the lysophospholipid solutions indicated in Table 5 below, at the concentration of 100 mg/L in 1% ethanol for 20 min. The control tomatoes were dipped in distilled water containing 1% ethol. After dipping, the fruits were stored at room temperature for 3 weeks. Production of ethylene gas was measured 7 days after treatment. The rate of ethylene production by the fruits gradually increased as the fruits started to ripen. While mature green at 0 day had no production of ethylene, the untreated control fruits produced ethylene at the rate of 1.26 $nl/g.hr^{-1}$ after 7 days of treatment (see Table 5 below). LPEegg-treated fruits showed production of ethylene similar to control. Whereas, both LPE (18:1) and LPI-treated fruits showed suppression of ethylene production, and this rate was only about half of the control, in LPEegg-treated fruits, suppression of ethylene production correlated prolonging shelf life of fruits. Consistent with this expectation, the percentages of rotten fruits after 3 weeks of incubation also indicated that LPE (18:1) and LPI are particularly more effective than LPEegg and the control in extending the shelf life of tomatoes. LPEsoy was found to be better than LPEegg in terms of prolonging the shelf-life of fruits (rotten fruits 24% in LPEegg and 15% in LPEsoy).

TABLE 5

| Treatment* | Ethylene Production after 7 days $(nl/g. hr^1)$ Mean ± SE** | Rotten fruits after 3 weeks (% of total) |
|---|---|---|
| Control | 1.26 ± 0.21 | 37.2 |
| LPEegg | 1.22 ± 0.22 | 24.4 |
| LPE18:1 | 0.70 ± 0.20 | 7.7 |
| LPI | 0.71 ± 0.40 | 17.5 |
| LPEsoy | 0.74 ± 0.10 | 15.0 |

*All solution were prepared in 1% (v/v) ethanol
**Data are mean ± SE of two independent experiments. Each experiment had 9 fruits per treatment.

EXAMPLE 4

Retardation of Ethephon-Induced Leaf Senescence

Ethephon, also known as Ethrel, (Ethrel is a trademark of Rhone-Poulenc Ag. Co. (Research Triangle Park, N.C.)) is an aqueous formulation that decomposes to ethylene and is used widely to maximize the yield of ripe tomato fruits in once-over harvesting operations. The present invention demonstrates that LPE (18:1) is superior to LPEegg and other lysophospholipids in protecting leaves from ethephon-induced leaf senescence. Tomato plants cv. H9144 were grown in a greenhouse for two and a half months to serve as sources of leaf samples. Plant were sprayed to runoff with ethephon at 1000 mg/L or with ethephon plus lysophospholipid mixtures as shown below in Table 6. Lysophospholipid solutions at 50 mg/L were prepared in 1% (v/v) ethanol and mixed with ethephon (1000 mg/L). Control plans were sprayed with ethephon alone in 1% (v/v) ethanol. Senescence of treated leaves was quantified 10 to 14 days after treatment by measuring chlorophyll and protein content. Ethephon-sprayed leaf tissue showed dramatic loss in chlorophyll and protein content as shown in Table 6 below. LPEegg significantly retarded ethephon-induced senescence. LPE (18:1) showed much better retardation of leaf senescence caused by ethephon. LPI had a little retarding effect on ethephon-induced leaf senescence. These results demonstrate that LPE (18:1) works even better than other forms of LPE for this purpose.

TABLE 6

| Treatment* | Chlorophyll Content (mg/g dry wt) Mean ± SE** | Protein Content (mg/g dry wt) Mean ± SE** |
|---|---|---|
| Ethephon (E) | 3.65 ± 0.25 | 58.8 ± 14.7 |
| E + LPEegg | 5.88 ± 2.04 | 81.9 ± 17.6 |
| E + LPE18:1 | 8.40 ± 2.70 | 100.0 ± 20.0 |
| E + LPI | 4.12 ± 0.55 | 60.0 ± 14.7 |

*All solution were prepared in 1% (v/v) ethanol.
**Data are mean ± SE of three independent experiments. Data were collected 10 to 14 days after treatment.

EXAMPLE 5

Enhancement of Fruit Ripening

This experiment was conducted to compare the effects of LPEegg, LPE (18:1) and LPI on fruit ripening. Tomato plants cv. H9478 were grown in pots for two and one-half months under fluorescent lights. Whole plants having about 10% of their fruits in the ripening stage were sprayed with a solution containing 100 mg/L of different lysophospholipids such as LPEegg, LPE (18:1) or LPI. All solutions contained 1% ethol and 0.05% sylgard 309 (Dow Corning Co., Midland, Mich.) as activating agents. Control plants received distilled water containing 1% ethanol and 0.05% sylgard 309. Fruits were harvested 10 days after treatment and graded into green, partial red, and red (indicating full ripening). LPEegg enhanced fruit ripening significantly compared to the control as previously disclosed in U.S. Pat. Nos. 5,126,155 and 5,110,341 (see Table 7). However, LPI and LPE (18:1) were found to be more effective than LPEegg. LPI and LPE (18:1) also enhanced fruit stability by prolonging shelf life of post harvest fruits compared to control and LPEegg (see Table 7).

TABLE 7

| Treatment* | At Harvest (weight % of total) | | | 3 Weeks After Harvest Soft Fruits (non marketable) (weight % of total) |
|---|---|---|---|---|
| | Green | Partial Red | Red | |
| Control | 33.2 | 13.2 | 53.6 | 47.8 |
| LPEegg | 22.8 | 15.9 | 61.3 | 36.6 |
| LPE18:1 | 22.9 | 11.7 | 65.4 | 33.0 |
| LPI | 18.3 | 11.7 | 70.1 | 25.6 |

*All solution were prepared in 1% (v/v) ethanol and 0.05 and sylgard 309. Spray applications were made 10 days before harvest.
**Data are average representing three independent experiments.

REFERENCES

1. Borochov, A., Halevy, A. H. & Shinitzky, M. (1982) *Plant Physiol.* 69, 296–299.
2. Fobel, M., Lynch, D. V. & Thompson, J. E. (1987) *Plant Physiol.* 85, 204–211.
3. Farag, K. M. & Palta, J. P. (1993) *Phsiol. Plant.* 87, 515–524.
4. Paliyath, G., Lynch, D. V. & Thompson, J. E. (1987) *Physiol. Plant.* 71, 503–511.
5. Thompson, J. E., Paliyath, G., Brown, J. H. & Duxbury, C. L. (1987) in *Plant Senescence: Its Biochemistry and Physiology,* eds. Thompson, W. W. & Northnagel, E. A., Huffaker, R. C. (The American Society of Plant Physiologists, Rockville, Md.), pp. 146–155.
6. Cheour, F., Arul, J., Makhlouf, J. & Willemot, C. (1992) *Plant Physiol.* 100, 1656–1660.

7. McCormac, D. J., Todd, J. F., Paliyath, G. & Thompson, J. E. (1993) *Plant Physiol. Biochem.* 31, 1–8.
8. Samama, A. M. & Pearce, R. S. (1993) *J. Exp. Bot.* 44, 1253–1265.
9. Voisine, R., Vezine, L.-P. & Willemot, C. (1993) *Plant Physiol.* 102, 213–218.
10. Ryu, S. B. & Wang, X. (1995) *Plant Physiol.* 108, 713–719.
11. Abousalbam, A., Riviere, M., Teissere, M. & Verger, R. (1993) *Biochim. Biophys. Acta* 1158, 1–7.
12. Lee, J. E. & Choi, M. U. (1996) *Bull. Korean Chem. Soc.* 17, 905–908.
13. Ryu, S. B. & Wang, X. (1996) *Biochim. Biophys.* Acta 1303, 243–250.
14. Ryu, S. B. Zheng, L. & Wang, X. (1996) *J. Am. Oil Chem. Soc.* 73, 1171–1176.
15. Rouser, G., Fleisher, S. & Yamamoto, A. (1970) *Lipids* 5, 494–496.
16. Farag, K. M. & Palta, J. P. (1993) *HortTechnology* 3, 62–65.
17. Dyer, J. H., Ryu, S. B. & Wang, X. (1994) *Plat Physiol.* 105, 715–724.
18. Kim, J. H., Suh, Y. J., Lee, t. G., Kim, Y., Bae, S. S., Kim, M. J., Lambeth, J. D., Suh, P.-G & Ryu, S. H. (1996) *J. Biol. Chem.* 271, 25213–25219.
19. Ryu, S. B., Karlsson, B. H., Ozgen, M. J. Palta J. P. (1997) *Proc. Natt. Acad. SCT. USA* 94, 12717–12721.
20. Kaur, M. N. & Palta, J. P. (1997) *HortScience.* 32, 888–890.

What is claimed is:

1. A method of delaying senescence in fruit and other plant tissues, the method comprising the step of applying to fruit or other plant tissues a composition comprising lysophosphatidylinositol, lysophosphatidylethanolamine (18:1) or combinations thereof.

2. The method of claim 1 wherein the composition further comprises an activating agent.

3. The method of claim 1 wherein the composition is an aqueous solution.

4. The method of claim 1 wherein the composition is applied before or after harvest.

5. The method of claim 1 wherein the composition contains an effective amount of lysophosphatidylinositol, lysophosphatidylethanolamine (18:1) or combinations thereof to delay senescence in fruit and other plant tissues.

6. The method of claim 1 wherein the composition contains from about 0.5 to about 1000 mg per liter of lysophosphatidylinositol, lysophosphatidylethanolamine (18:1) or combinations thereof.

7. The method of claim 2 wherein the activating agent is ethanol, a nonylphenol polyoxyethylene ether or a siloxylated polyether.

8. A method of enhancing the ripening and stability of fruits the method comprising the step of applying preharvest to whole plant tissues a composition comprising lysophosphatidylinositol, lysophosphatidylethanolamine (18:1) or combinations thereof.

9. The method of claim 8 wherein the composition further comprises an activating agent.

10. The method of claim 8 wherein the composition is an aqueous solution.

11. The method of claim 8 wherein the composition contains an effective amount of lysophosphatidylinositol, lysophosphatidylethanolamine (18:1) or combinations thereof to enhance ripening and stability of fruit.

12. The method of claim 8 wherein the composition contains from about 0.5 to about 1000 mg per liter of lysophosphatidylinositol, lysophosphatidylethanolamine (18:1) or combinations thereof.

13. The method of claim 9 wherein the activating agent is ethanol, a nonylphenol polyoxyethylene ether or a siloxylated polyether.

* * * * *